United States Patent
Hirosawa

(10) Patent No.: US 9,259,140 B2
(45) Date of Patent: Feb. 16, 2016

(54) ENDOSCOPE APPARATUS IN WHICH THE WAVEFORM OF A RESET GATE SIGNAL INCLUDED IN A DRIVE SIGNAL FOR AN IMAGE PICKUP DEVICE IS CHANGED BASED ON TEMPERATURE

(71) Applicant: OLYMPUS CORPORATION, Shibuya-ku, Tokyo (JP)

(72) Inventor: Masahiro Hirosawa, Sayama (JP)

(73) Assignee: OLYMPUS CORPORATION, Tokyo (JP)

( * ) Notice: Subject to any disclaimer, the term of this patent is extended or adjusted under 35 U.S.C. 154(b) by 283 days.

(21) Appl. No.: 13/891,756

(22) Filed: May 10, 2013

(65) Prior Publication Data
US 2014/0307071 A1    Oct. 16, 2014

(30) Foreign Application Priority Data
Apr. 12, 2013    (JP) .................................. 2013-084306

(51) Int. Cl.
| H04N 7/18 | (2006.01) |
| A61B 1/00 | (2006.01) |
| A61B 1/045 | (2006.01) |
| A61B 1/12 | (2006.01) |
| G02B 23/24 | (2006.01) |
| H04N 5/357 | (2011.01) |
| H04N 5/363 | (2011.01) |
| H04N 5/376 | (2011.01) |
| H04N 5/225 | (2006.01) |

(52) U.S. Cl.
CPC ............. *A61B 1/00133* (2013.01); *A61B 1/045* (2013.01); *A61B 1/128* (2013.01); *G02B 23/2484* (2013.01); *G02B 23/2492* (2013.01); *H04N 5/3575* (2013.01); *H04N 5/363* (2013.01); *H04N 5/3765* (2013.01); *H04N 2005/2255* (2013.01)

(58) Field of Classification Search
CPC ..................... A61B 2018/00642; A61B 1/045; A61B 1/05; H04N 2005/2255
See application file for complete search history.

(56) References Cited

U.S. PATENT DOCUMENTS

| 5,031,036 A * | 7/1991 | Kikuchi et al. .................. 348/71 |
| 2004/0171915 A1* | 9/2004 | Glukhovsky et al. .......... 600/160 |
| 2007/0112247 A1* | 5/2007 | Hirata ............................ 600/101 |
| 2008/0122942 A1* | 5/2008 | Mimata et al. ............. 348/222.1 |
| 2008/0158348 A1* | 7/2008 | Karpen et al. ................... 348/82 |
| 2012/0167882 A1* | 7/2012 | Wood et al. ............... 128/204.17 |
| 2013/0035545 A1* | 2/2013 | Ono .............................. 600/109 |

FOREIGN PATENT DOCUMENTS

JP          08-018871 A     1/1996

* cited by examiner

*Primary Examiner* — Victor Kostak
(74) *Attorney, Agent, or Firm* — Holtz, Holtz & Volek PC

(57) ABSTRACT

An endoscope apparatus is an endoscope apparatus having an insertion portion having an image pickup device in a distal end portion, and a main body portion, and has a drive circuit that outputs a drive signal that drives the image pickup device, and a changing section that changes at least one of a pulse width and a peak value of a reset gate signal included in the drive signal, in response to a temperature of a vicinity of the image pickup device or the main body portion.

15 Claims, 12 Drawing Sheets

TBL1

| TEMPERATURE | PULSE WIDTH |
|---|---|
| 100 DEGREES OR MORE | 10nsec |
| 50 DEGREES OR MORE AND LESS THAN 100 DEGREES | 8nsec |
| 20 DEGREES OR MORE AND LESS THAN 50 DEGREES | 5nsec |
| LESS THAN 20 DEGREES | 2nsec |

FIG. 7

TBL2

| TEMPERATURE | PEAK VALUE |
|---|---|
| 100 DEGREES OR MORE | 3.6V |
| 50 DEGREES OR MORE AND LESS THAN 100 DEGREES | 3.4V |
| 20 DEGREES OR MORE AND LESS THAN 50 DEGREES | 3.2V |
| LESS THAN 20 DEGREES | 3.0V |

| TEMPERATURE | PULSE WIDTH | PEAK VALUE |
|---|---|---|
| 100 DEGREES OR MORE | 9nsec | 3.5V |
| 50 DEGREES OR MORE AND LESS THAN 100 DEGREES | 7nsec | 3.3V |
| 20 DEGREES OR MORE AND LESS THAN 50 DEGREES | 4nsec | 3.1V |
| LESS THAN 20 DEGREES | 1nsec | 2.9V |

ENDOSCOPE APPARATUS IN WHICH THE WAVEFORM OF A RESET GATE SIGNAL INCLUDED IN A DRIVE SIGNAL FOR AN IMAGE PICKUP DEVICE IS CHANGED BASED ON TEMPERATURE

CROSS REFERENCE TO RELATED APPLICATION

This application claims the benefit of Japanese Application No. 2013-084306 filed in Japan on Apr. 12, 2013, the contents of which are incorporated herein by this reference

BACKGROUND OF THE INVENTION

1. Field of the Invention

The present invention relates to an endoscope apparatus having an image pickup device in a distal end portion of an insertion portion.

2. Description of the Related Art

Conventionally, endoscope apparatuses have been widely used in an industrial field and a medical field. An image pickup device is disposed at a distal end of an insertion portion, and an endoscopie image obtained by an image being picked up by the image pickup device is displayed on a display apparatus of a main body portion that is connected to the insertion portion.

Endoscope apparatuses have elongated insertion portions, and are used under various temperature environments such as inspection of the insides of jet engines under high-temperature environments, and inspection of water pipes in cold districts.

It becomes difficult for image pickup devices such as a charge coupled device (hereinafter, called CCD) of recent years to sample image signals that are video signals stably due to high frequency drive accompanying increase in density of pixels, and variations in signal waveforms of output signals (for example, called CCDout) that are outputted from the image pickup devices accompanying temperatures. For the purpose of temperature compensation, for example, Japanese Patent Application Laid-Open Publication No. 8-18871 proposes the art of correcting the intensity change of the video signal which is outputted by the CCD by gain adjustment based on the temperature.

Since endoscope apparatuses are used under various temperature environments, stable image qualities are required as inspection apparatuses in the use environments at various temperatures.

SUMMARY OF THE INVENTION

An endoscope apparatus of one aspect of the present invention is an endoscope apparatus having an insertion portion having an image pickup device in a distal end portion, and a main body portion, and has a drive circuit that outputs a drive signal that drives the image pickup device, and a changing section that changes at least one of a pulse width and a peak value of a reset gate signal included in the drive signal, in response to a temperature of a vicinity of the image pickup device or the main body portion.

BRIEF DESCRIPTION OF THE DRAWINGS

FIG. 7 is a diagram showing an example of a table TBL2 that is stored in the memory section 29 according to a second embodiment of the present invention;

DETAILED DESCRIPTION OF THE PREFERRED EMBODIMENTS

Hereinafter, embodiments of the present invention will be described with use of the drawings.

(First Embodiment)

Figure 1:
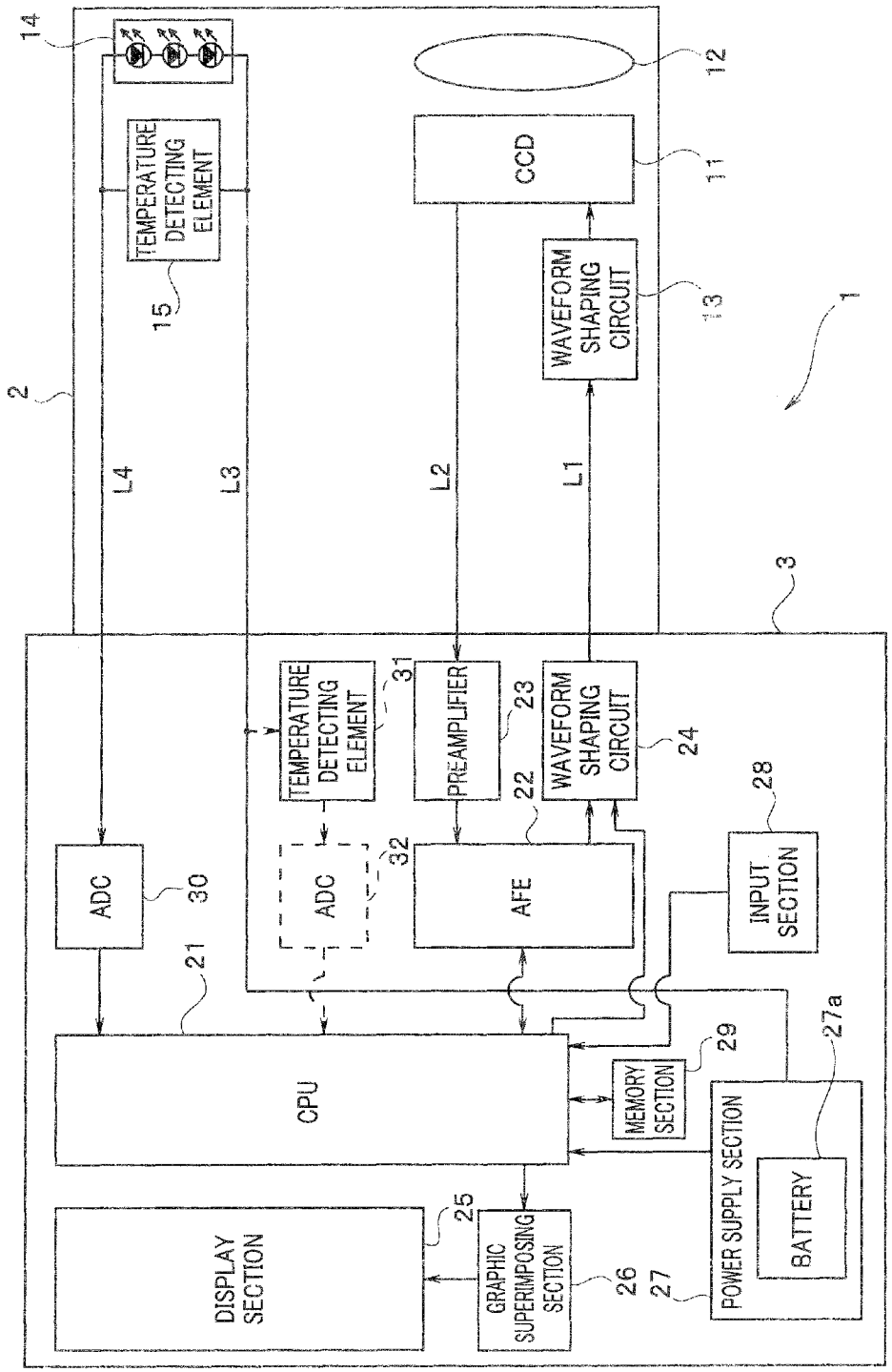
FIG. 1 is a configuration diagram of an endoscope apparatus according to a first embodiment of the present invention.

FIG. 1 is a configuration diagram of an endoscope apparatus according to a first embodiment of the present invention.

An endoscope apparatus 1 is configured by having an elongated insertion portion 2, and a main body portion 3 to which a proximal end of the insertion portion 2 is connected. In a distal end portion of the insertion portion 2, a CCD 11 as an image pickup device, and an objective optical system 12 for forming an image of an object on an image pickup surface of the CCD 11 are provided. A drive signal is inputted to the CCD 11 via a waveform shaping circuit 13 through a signal line L1. An image pickup signal of the CCD 11 is outputted through a signal line L2. Namely, the endoscope apparatus 1 has the insertion portion 2 having the image pickup device in the distal end portion, and the main body portion 3.

Further, an illumination section 14 including a plurality of light emitting diodes (hereinafter called LEDs) is provided at the distal end portion of the insertion portion 2. Illuminating light of the illumination section 14 is emitted from the distal end portion of the insertion portion 2 via an optical system for illumination not illustrated.

A temperature detecting element 15 for detecting a temperature of a vicinity of the CCD 11 is provided at the distal end portion of the insertion portion 2. The temperature detecting element 15 is a temperature sensor such as a thermistor, and the illumination section 14 and the temperature detecting element 15 receive supply of a power supply from signal lines L3 and L4.

The CCD 11 reads a charge corresponding to a light from a target illuminated by the illumination section 14 that is a light source, and outputs an output signal CCDout that is a video signal.

The main body portion 3 is configured by including a central processing unit (hereinafter, called a CPU) 21, an analog front end section (hereinafter, called an ALE section) 22, a preamplifier 23, a waveform shaping circuit 24, a display section 25, a graphic superimposing section 26, a power supply section 27, an input section 28, a memory section 29, and an analogue-digital converting circuit (hereinafter, called an ADC circuit) 30.

The CPU 21 is a control section for executing control of the whole of the endoscope apparatus 1 and specified functions. The CPU 21 also performs control of changing a pulse width of a pulse signal that drives the CCD 11 in response to a temperature, as will be described later.

The AFE, section 22 is a circuit that includes a timing generator, a CDS circuit and the like, drives the CCD 11, processes an image pickup signal that is a video signal from the CCD 11 and outputs an image signal to the CPU 21, as will be described later. A configuration of the AFE 22 will be described later.

The preamplifier 23 is an amplifier that amplifies the output signal CCDout from the CCD 11. The preamplifier 23 amplifies the output signal (CCDout) of the CCD 11 that is attenuated by the length of the signal cable that is inserted through an inside of the insertion portion 2.

The waveform shaping circuit 24 is a circuit that shapes waveforms of various drive signals such as horizontal synchronization signals that are outputted from the AFE 22.

Further, the waveform shaping circuit 24 can change peak values of the waveforms of various drive signals based on a set point signal from the CPU 21. Therefore, as shown in FIG. 1, the waveform shaping circuit 24 is configured so that the signal from the CPU 21 is inputted therein.

The display section 25 is a display apparatus such as a liquid crystal display device that displays an endoscopic image and various menu screens.

The graphic superimposing section 26 is a circuit for superimposing a graphic image such as a menu screen generated in the CPU 21 onto an endoscopic image.

The power supply section 27 is a circuit that includes a battery 27a, and supplies power supply to the respective sections in the endoscope apparatus 1.

The input section 28 is an input apparatus such as an operation section having various buttons and a touch panel provided at the display section 25, and outputs an inputted signal, data and the like to the CPU 21.

The memory section 29 includes a nonvolatile memory (for example, a hard disk apparatus, and a flash memory) that stores various programs that the CPU 21 executes and data necessary for execution of the respective programs.

The ADC circuit 30 is a circuit that converts a voltage or the like corresponding to the temperature detected in the temperature detecting element 15 provided at the insertion portion 2 into a digital signal, and outputs the digital signal to the CPU 21. Namely, the CPU 21 can obtain temperature information of the distal end portion of the insertion portion 2 from the output signal of the ADC circuit 30.

Note that when the endoscope apparatus 1 is used in such a situation that the temperature of the distal end portion of the insertion portion 2 and an ambient temperature of the main body portion 3 are the same, the temperature detecting element may be provided in the main body portion 3. In the case, the temperature detecting element 31, and the ADC circuit 32 which converts the analog signal of the temperature detecting element 31 into a digital signal are provided in the main body portion 3, and the CPU 21 can obtain temperature information of the main body portion 3 from the ADC circuit 32, as shown by the dotted lines in FIG. 1.

Furthermore, in FIG. 1, the waveform shaping circuit 13 is provided at an input stage of the CCD 11 in the distal end portion of the insertion portion 2, and the waveform shaping circuit 24 is further provided at an output stage of the AFE section 22, but when the insertion portion 2 is not long, only either one of the waveform shaping circuits 24 and 13 may be provided.

Figures 2, 3:
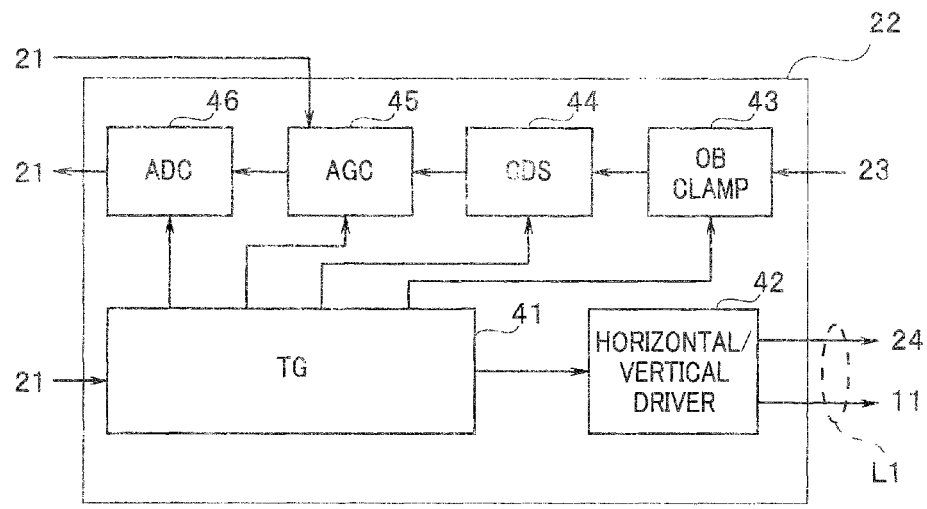
FIG. 2 is a block diagram showing a configuration of an AFE section 22 according to the first embodiment of the present invention.
FIG. 3 is a diagram showing an example of a table TBL1 that is stored in a memory section 29 according to the first embodiment of the present invention.

FIG. 2 is a block diagram showing the configuration of the AFE section 22. The AFE section 22 has a timing generator (hereinafter, called TG) 41, a horizontal/vertical driver 42, an OB clamp circuit 43, a correlated double sampling circuit (hereinafter, called a CDS circuit) 44, an auto gain control circuit (hereinafter, called an AGC circuit) 45 arid an ADC circuit 46.

The TG 41 is a circuit that generates and outputs various timing signals for use in the respective sections in the AFE section 22.

The horizontal/vertical driver 42 outputs horizontal synchronization signals and vertical synchronization signals based on the timing signal from the TG 41. Here, a reset gate signal RG and a horizontal transfer signal 11 as the horizontal synchronization signals are outputted to the waveform shaping circuit 24. The vertical synchronization signals are outputted to the CCD 11. Namely, the horizontal/vertical driver 42 configures a drive circuit that outputs a drive signal that drives the CCD 11 which is an image pickup device.

The horizontal/vertical driver 42 includes a drive IC, a DC bias circuit, a differentiating circuit and the like, and performs waveform shaping of the horizontal transfer signal H and the reset gate signal RG and outputs the horizontal transfer signal 11 and the reset gate signal RG, in order to drive the CCD 11 properly.

The OB clamp circuit 43 is a circuit that clamps electric charges of an OB (optical black) region of the CCD 11, and reproduces a signal of a black level.

The CDS circuit 44 is a circuit that performs correlated double sampling. The CDS circuit removes amplification noise and reset noise of the output signal (CCDout) based on a sample-and-hold pulse (hereinafter, called an SHP signal) by which a feedthrough time period of the output signal (CCDout) of the CCD 11 is clamped, and a sample-and-hold pulse (hereinafter, called an SHD signal) by which a signal time period is clamped. The SHP signal and the SHD signal are inputted to the CDS circuit 44 from the TG 41.

The AGC circuit 45 is a circuit that performs automatic adjustment of gain with respect to an input signal. Setting data is inputted to the AGC circuit 45 from the CPU 21, and automatic adjustment of gain is performed. The AGC circuit 45 increases gain of an image signal of a dark object, and matches the amplitude of the output signal (CCDout) with a dynamic range of the ADC circuit 46 in the rear stage.

The ADC circuit 46 is a circuit that converts an analog signal inputted from the AGC circuit 45 into a digital signal.

FIG. 3 is a diagram showing an example of a table TBL1 that is stored in the memory section 29.

The table TBL1 is a data table in which data of the pulse width values of the reset signal RG corresponding to temperatures is set. Here, data, in which the pulse widths of the reset gate signal RG are set at 0 nsec (nanosecond), 8 nsec, 5 nsec and 2 nsec respectively in response to four cases of a case of the temperature detected by the temperature detecting element 15 being 100 degrees or more, a case of the temperature being 50 degrees or more and less than 100 degrees, a case of the temperature being 20 degrees or more and less than 50 degrees, and a case of the temperature being less than 20 degrees, is registered in the table TBL1.

Here, an example of how the output signal CCDout of the CCD 11 changes in accordance with a temperature will be described at first.

Figure 4:
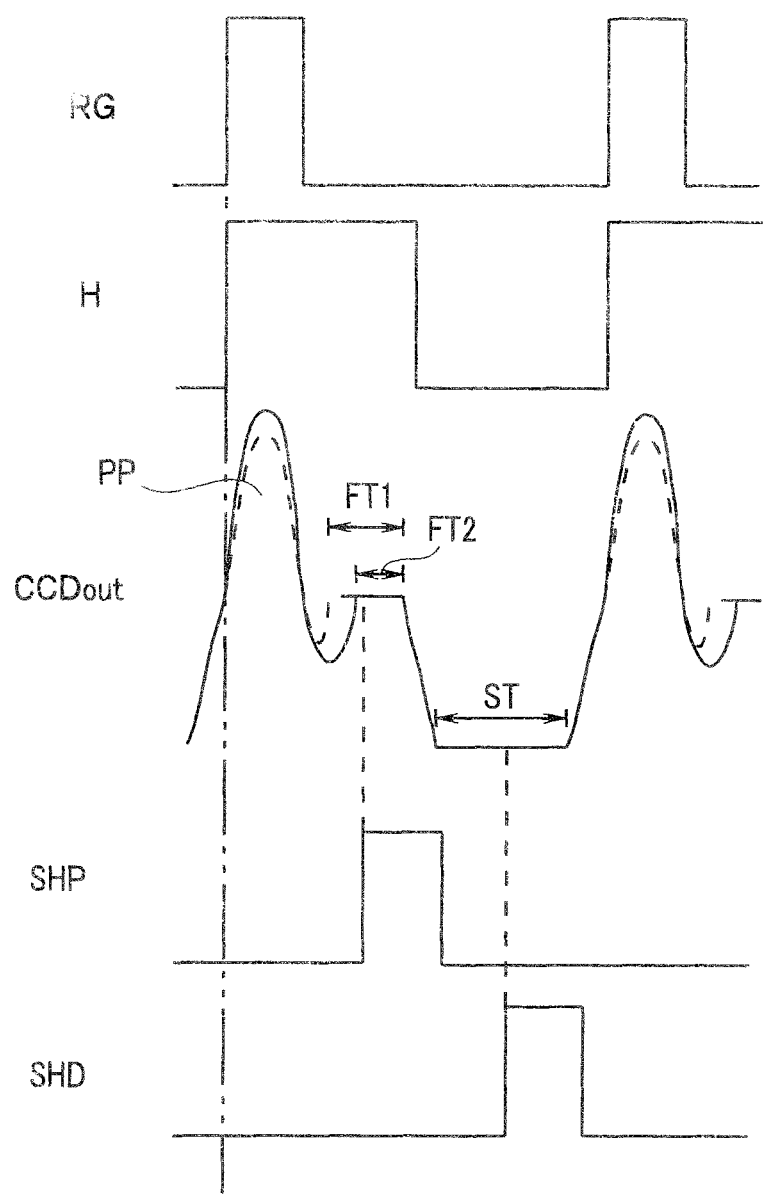
FIG. 4 is a waveform chart showing a relationship of horizontal synchronization signals, an output signal CCDout of a CCD 11, an SHP signal, and an SHD signal.

FIG. 4 is a waveform chart showing a relationship of the horizontal synchronization signals, the output signal CCDout of the CCD 11, the SHP signal and the SHD signal.

In response to input of the reset gate signal RG and the horizontal transfer signal H which are the horizontal synchronization signals, the CCD 11 outputs the output signal CCDout which is a video signal. At this time, the output signal CCDout has a through pulse portion PP corresponding to the reset gate signal. The reset gate signal RG is a signal that is outputted by being superimposed on the output signal CCDout of the CCD 11 which is an image pickup device. Further, the output signal CCDout has a feedthrough time period FT and a signal time period ST after the through pulse portion PP.

The SHP signal and the SHD signal are outputted at predetermined stable timing of each of the feedthrough time period FT and the signal time period ST, whereby the CDS circuit 44 can clamp a voltage for correlated double sampling.

The CCD 11 has the characteristic that the waveform of the through pulse portion PP of the output signal CCDout becomes higher than a waveform at a time of a normal temperature shown by the dotted line when the temperature of the CCD 11 becomes low. This is due to the temperature characteristic of the CCD 11 itself or the temperature characteristic of the drive circuit including the waveform shaping circuit 13.

When a peak value of the through pulse signal PP like this becomes high, undershoot in the waveform following the through pulse portion PP becomes large, and the feedthrough time period FT becomes short. FIG. 4 shows that a feedthrough time period FT2 at the time of the peak value of the through pulse signal PP being high is shorter than the feedthrough time period FT1 of the through pulse signal PP at the time of a normal temperature shown by the dotted line.

When the feedthrough time period FT becomes short like this, there arises the fear that the reference potential cannot be sampled and held stably in the CDS circuit.

Thus, in the present embodiment, the CPU 21 uses the data of the table TBL1, and adjusts the pulse width of the reset gate signal RG in response to the temperature, and thereby, changes the waveform of the reset gate signal RG so that the feedthrough time period FT does not become short.

Figure 5:
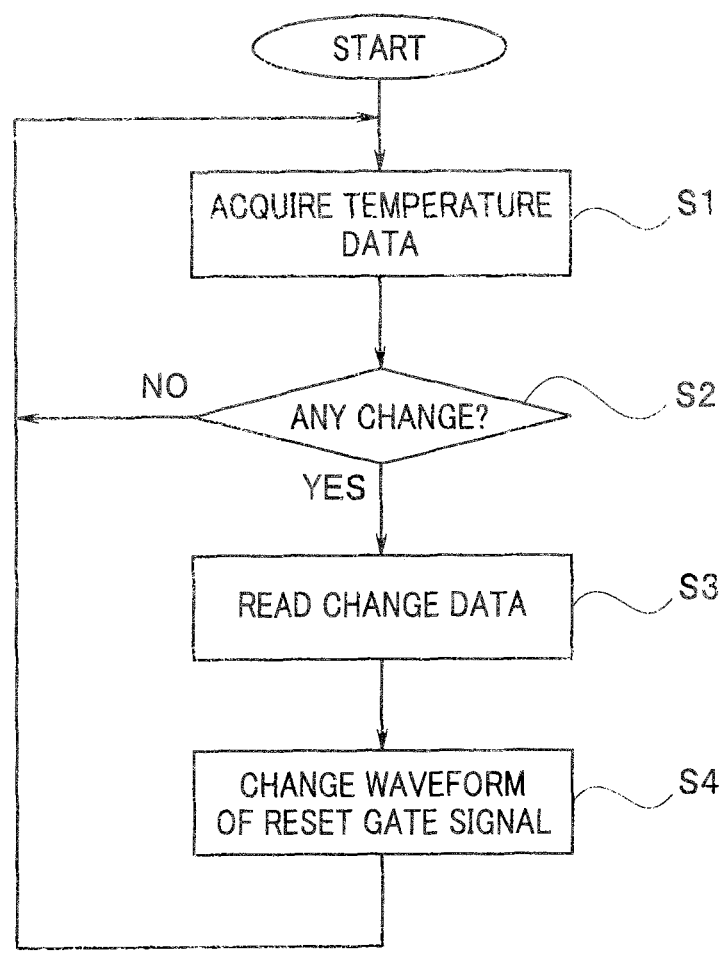
FIG. 5 is a flowchart showing an example of a flow of processing of hanging a waveform of a reset gate signal RG by a CPU 21, according to the first embodiment of the present invention.

FIG. 5 is a flowchart showing an example of a flow of processing of changing the waveform of the reset gate signal RG by the CPU 21.

The CPU 21 acquires the temperature data of the CCD 11 detected by the temperature detecting element 15 via the ADC circuit 30 (S1) The temperature detecting element 15 is provided in the vicinity of the CCD 11 to detect the temperature of the vicinity of the CCD 11, and therefore, the temperature data acquired in S1 is substantially the temperature data of the CCD 11. Note that as described above, in the case of the temperature detecting element 31, the temperature detecting element 31 is provided at the main body portion 3 to detect the temperature of the main body portion 3, and therefore, the temperature data acquired in Si is the temperature data of the main body portion 3.

Next, the CPU 21 determines whether or not there is any change in the temperature from the acquired temperature data (S2). The determination is performed based on whether or not a temperature range of the table TBL1 to which the temperature previously acquired belongs and a temperature range to which the present temperature acquired this time belongs differ from each other. For example, if the temperature previously acquired is 25 degrees, and the temperature acquired this time is 24 degrees, the two temperatures are in the same temperature range (range of more than 20 degrees and less than 50 degrees) of the table TBL1, and therefore, it is determined that there is no change in the temperature (S2: NO). Further, for example, if the temperature previously acquired is 20 degrees, and the temperature acquired this time is 19 degrees, the temperature previously acquired is in the temperature range (20 degrees or more and less than 50 degrees) of the table TBL1, but the temperature acquired this time is in the temperature range (range of less than 20 degrees) of the table TBL1, and therefore, it is determined that there is a change in the temperature (S2: YES).

Note that at the initial time, the temperature data previously acquired is absent, and therefore, it is determined that there is a temperature change.

When there is no change in temperature (S2: NO), the process returns to S1. When there is a change in temperature (S2: YES), the CPU 21 reads the change data of the pulse width corresponding to the temperature acquired this time from the table TBL1 (S3).

For example, in the case of FIG. 3, if the temperature acquired this time is less than 20 degrees, "2 nsec" is read from the table TBL1 of the memory section 29 as change data.

Subsequently, the CPU 21 changes the waveform of the reset gate signal RG by using the change data (S4). Change of the waveform of the reset gate signal RG is performed by the CPU 21 giving the change data of the pulse width of the reset gate signal RG to the TG 41, and the TG 41 generating the reset gate signal RG based on the change data of the pulse width. After S4, the process returns to S1.

Consequently, the CPU 21 and the TG 41 configure a changing section that changes the pulse width of the reset gate signal RG which is included in the horizontal synchronization signals that are drive signals, in response to the temperature of the vicinity of the CCD 11 or the main body portion 3. Further, the memory section 29 configures a storage section in which the change values which are for changing the pulse width, and correspond to temperatures are stored. Subsequently, the CPU 21 which is the changing section refers to the table TBL1 of the memory section 29, reads the change value corresponding to the temperature and changes the pulse width based on the read change value.

Note that in the table TBL1, the change values themselves are set, but correction values with respect to a predetermined reference value may be set to be stored. The CPU 21 changes the pulse width based on the correction value.

Figure 6:
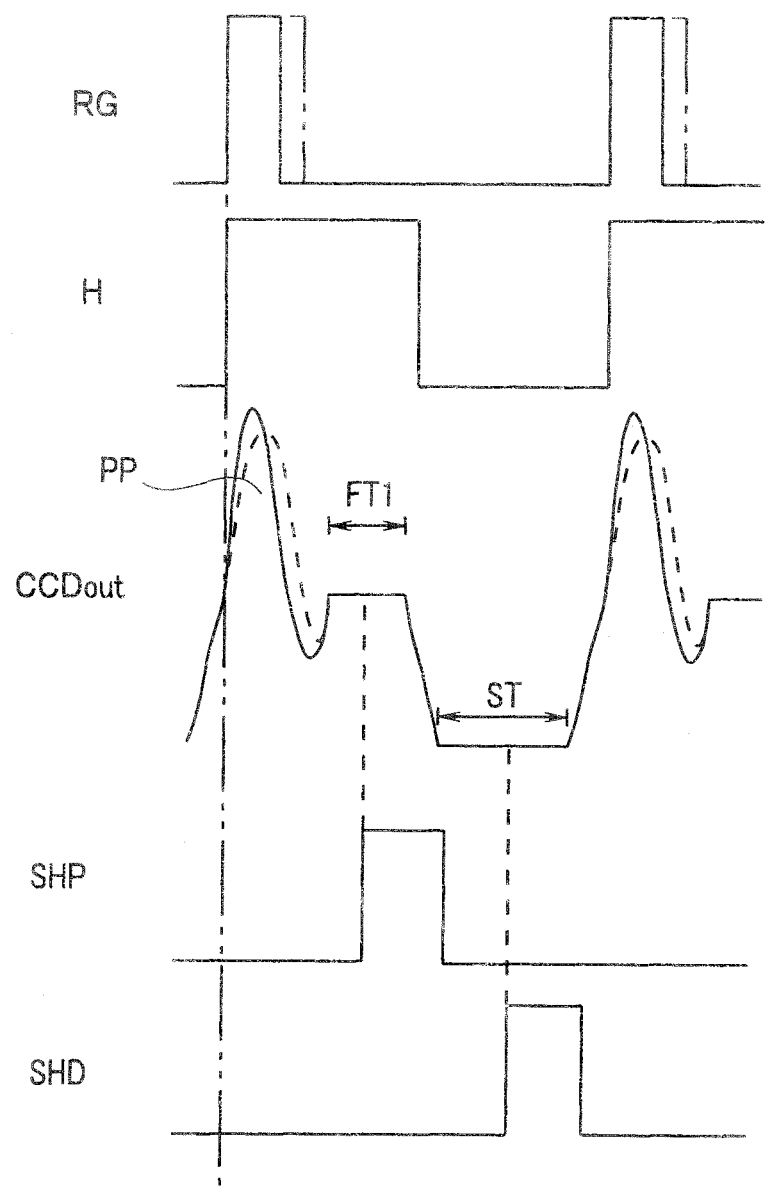
FIG. 6 is a waveform chart showing a relationship of the horizontal synchronization signals, the output signal CCDout of the CCD 11, the SHP signal and the SHD signal when a pulse width of the reset gate signal RG is changed, according to the first embodiment of the present invention.

FIG. 6 is a waveform chart showing a relationship of the horizontal synchronization signals, the output signal CCDout of the CCD 11, the SHP signal and the SHD signal when the pulse width of the reset gate signal RG is changed.

For example, as shown in FIG. 6, when the pulse width of the reset gate signal RG becomes short, a width of the through pulse PP becomes narrow As a result, the feedthrough time period FT becomes the same as a feedthrough time period FT1 at the time of a normal temperature Namely, in the table TBL1, the data of the pulse width of the reset gate signal RG is set and registered so that the feedthrough time period FT becomes the same as the feedthrough time period FT1 at the time of a normal temperature, in response to the temperature, and the CPU 21 changes the pulse width of the reset gate signal RG in response to the temperature of the CCD 11 which is detected.

As a result, the reference potential can be stably sampled and held in the CDS circuit 44, as a result of which, amplification noise and reset noise are properly removed, and high endoscopic image quality with less noise can be obtained.

(Second Embodiment)

In the first embodiment, the pulse width of the reset gate signal RG is adjusted in response to the temperature, whereas n a second embodiment, the peak value of the reset gate signal RG is adjusted in response to the temperature.

Since a configuration of an endoscope apparatus of the second embodiment is substantially the same as the configuration of the endoscope apparatus of the first embodiment, the same reference signs are used for the same components, and only different components will be described.

FIG. 7 is a diagram showing an example of a table TBL2 that is stored in the memory section 29.

The table TBL2 is a data table in which data of the peak values of the reset gate signal RG corresponding to temperatures is set Here, data, in which the peak values of the reset gate signal RG are set at 3.6 V (volt), 3.4 V, 3.2 V and 3.0 V respectively in response to four cases of a case of the temperature detected by the temperature detecting element 15 being 100 degrees or more, a case of the temperature being 50 degrees or more and less than 100 degrees, a case of the temperature being 20 degrees or more and less than 50 degrees, and a case of the temperature being less than 20 degrees, is registered in the table TBL2.

Processing of changing the waveform of the reset gate signal RG by the CPU 21 in the present embodiment is similar to the processing of FIG. 5. In S3 of FIG. 5 the change data is read from the table TBL2, and in S4, the peak value of the waveform of the reset gate signal RG is changed. Change of the waveform of the reset gate signal RG is performed by the CPU 21 giving the change date of the peak value of the reset gate signal RG to the waveform shaping circuit 24, and the waveform shaping circuit 24 generating the reset gate signal RG based on the change data of the peak value.

Accordingly, the CPU 21 and the waveform shaping circuit 24 configure a changing section that changes the peak value of the reset gate signal RG that is included in the horizontal synchronization signals that are drive signals in response to the temperature of the vicinity of the CCD 11 or the main body portion 3. Further, the memory section 29 configures a storage section in which the change value which is for changing the peak value and corresponds to the temperature is stored. Subsequently, the CPU 21 which is the changing section refers to the table TBL2 of the memory section 29, reads the change value corresponding to the temperature, and changes the peak value based on the read change value.

Note that in the table TBL2, the change values themselves are set, but correction values with respect to a predetermined reference value may be set to be stored. The CPU 21 changes the peak value based on the correction value.

Figure 8:
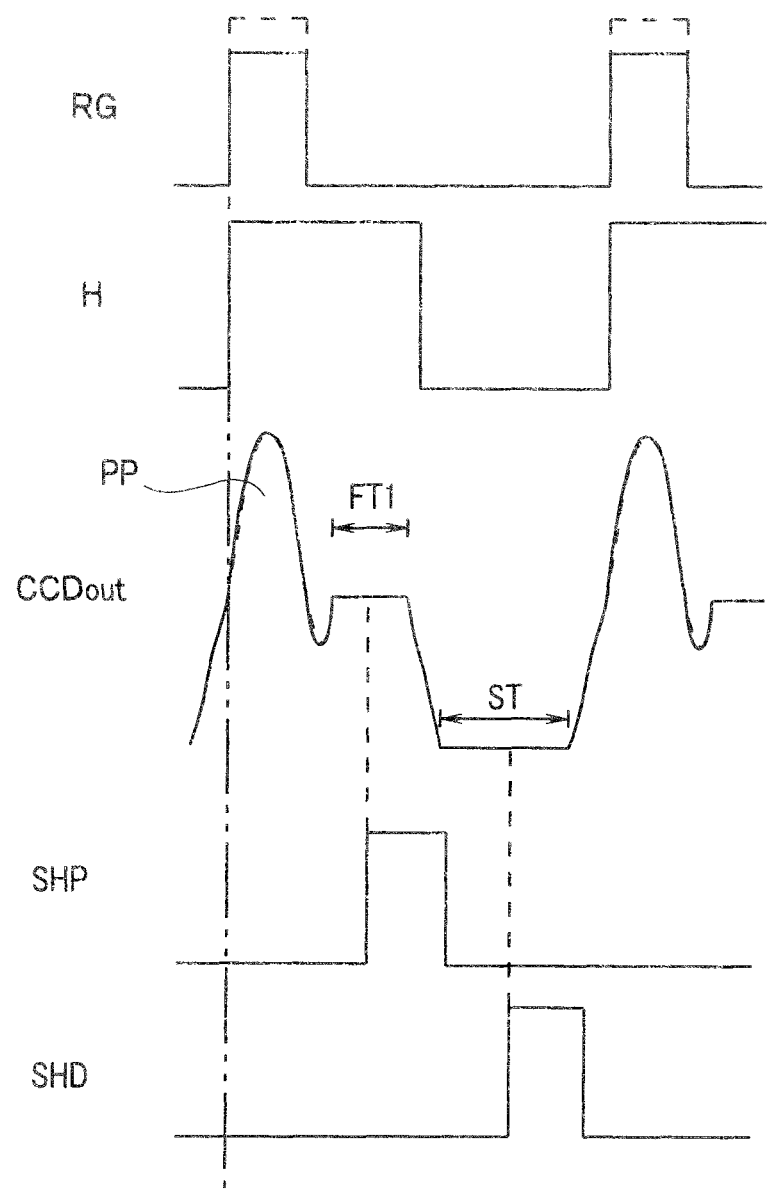
FIG. 8 is a waveform chart showing a relationship of the horizontal synchronization signals, the output signal CCDout of the CCD 11, the SHP signal and the SHD when a peak value of the reset gate signal RG is changed, according to the second embodiment of the present invention.

FIG. 8 is a waveform chart showing a relationship of the horizontal synchronization signals, the output signal CCDout of the CCD 11, the SHP signal and the SHD signal when the peak value of the reset gate signal RG is changed.

For example, as shown in FIG. 8, when the peak value of the reset gate signal RG becomes lower than the peak value at a time of a normal temperature shown by the dotted line, a peak value of the through pulse PP reduces, and undershoot also decreases. As a result, the feedthrough time period FT becomes the same as the feedthrough time period FT1 at the time of a normal temperature.

Namely, in the table TBL2, the data of the peak values of the reset gate signal RG are set and registered so that the feedthrough time period FT becomes the same as the feedthrough time period FT1 at the time of a normal temperature, in response to the temperatures, and the CPU 21 changes the peak value of the reset gate signal RG in response to the temperature of the CCD 11 which is detected.

As a result, the reference potential can be stably sampled and held in the CDS circuit 44, as a result of which, amplification noise and reset noise arc properly removed, and high endoscopic image quality with less noise can be obtained.

(Third Embodiment)

In the first embodiment, the pulse width of the reset gate signal RG is adjusted in response to a temperature, and in the second embodiment, the peak value of the reset gate signal RG is adjusted in response to a temperature, whereas in the present embodiment, both of the pulse width and the peak value of the reset gate signal RG are adjusted in response to a temperature.

Figure 9:
FIG. 9 is a diagram showing an example of a table TBL3 that is stored in the memory section 29 according to a third embodiment of the present invention.

Since a configuration of an endoscope apparatus of the third embodiment is substantially the same as the configuration of the endoscope apparatus of the first embodiment, the same reference signs are used for the same components, and only different components will be described, FIG. 9 is a diagram showing an example of a table TBL3 stored in the memory section 29.

The table TBL3 is a data table in which data of the pulse widths and the peak values of the reset gate signal RG corresponding to temperatures is set. Here, data, in which the pulse widths and the peak values of the reset gate signal RG are set at 9 nsec and 3.5 V. 7 nsec and 3.3 V, 4 nsec and 3.1 V, and 1 nsec and 29 V respectively in response to four cases of a case of the temperature detected by the temperature detecting element 15 being 100 degrees or more, a case of the temperature being 50 degrees or more and less than 100 degrees, a ease of the temperature being 20 degrees or more and less than 50 degrees, and a case of the temperature being less than 20 degrees, is registered in the table TBL3.

Note that in the table TBL3, the change values themselves are set, but correction values with respect to a predetermined reference value may he set to be stored. The CPU 21 changes the pulse width and the peak value based on the correction values, Processing of changing the waveform of the reset gate signal RG by the CPU 21 in the present embodiment is similar to the processing of FIG. 5. In S3 of FIG. 5, the change data is read from the table TBL3, and in S4, the pulse width and the peak value of the waveform of the reset gate signal RG are changed. Change of the waveform of the reset gate signal RG is performed by the CPU 21 giving the change date of the pulse width of the reset gate signal RG to the TG 41, and giving the change data of the peak value to the waveform shaping circuit 24, and the TG 41 and the waveform shaping circuit 24 respectively generating the reset gate signals RG based on the change data of the pulse width and the peak value.

Figure 10:
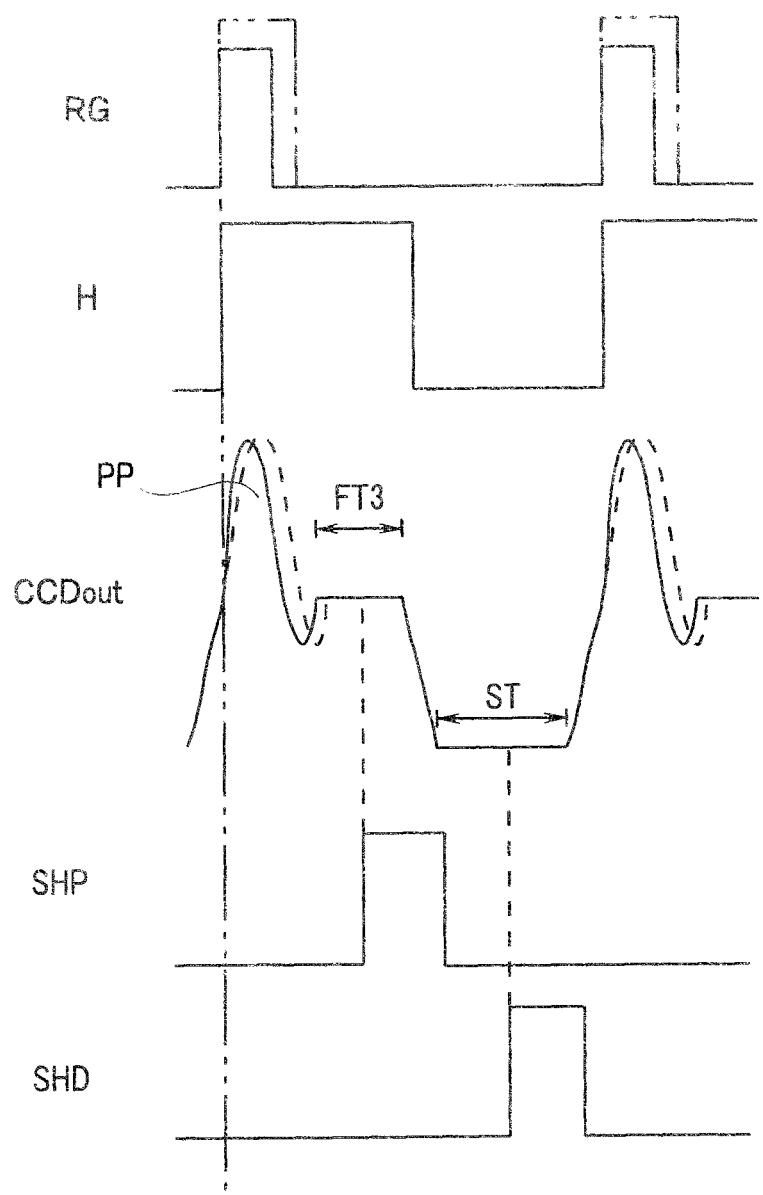
FIG. 10 is a waveform chart showing a relationship of the horizontal synchronization signals, the output signal CCDout of the CCD 11, the SHP signal and the SHD signal when the pulse width and the peak value of the reset gate signal RG are changed, according to the third embodiment of the present invention.

FIG. 10 is a waveform chart showing a relationship of the horizontal synchronization signals, the output signal CCDout of the CCD 11, the SHP signal and the SHD signal when the pulse width and the peak value of the reset gate signal RG are changed, For example, as shown in FIG. 10, when the pulse width and the peak value of the reset gate signal RG become shorter than the pulse width and lower than the peak value at a time of a normal temperature shown by the dotted line, a peak value of the through pulse PP does not rise, and undershoot does not decrease, either. As a result, the feedthrough time period FT becomes longer than the feedthrough time period FT1 at the time of a normal temperature (FT3).

Namely, in the table TBL3, the data of the pulse widths and the peak values of the reset gate signal RG is registered so that the feedthrough time period FT becomes the same as the feedthrough time period FT1 at the time of a normal temperature, in response to the temperatures, and the CPU 21 changes the pulse width and the peak value of the reset gate signal RG in response to the temperature of the CCD 11 which is detected.

As a result, the reference potential can be stably sampled and held in the CDS circuit 44, as a result of which, amplification noise and reset noise are properly removed, and high endoscopic image quality with less noise can be obtained.

(Fourth Embodiment)

In the first to the third embodiments described above, the temperature of the vicinity of the image pickup device or the temperature of the main body portion in the endoscope apparatus is detected with use of the temperature detecting device such as a thermistor, whereas in a fourth embodiment, the temperature of the image pickup device is detected without use of a thermistor or the like.

Figure 11:
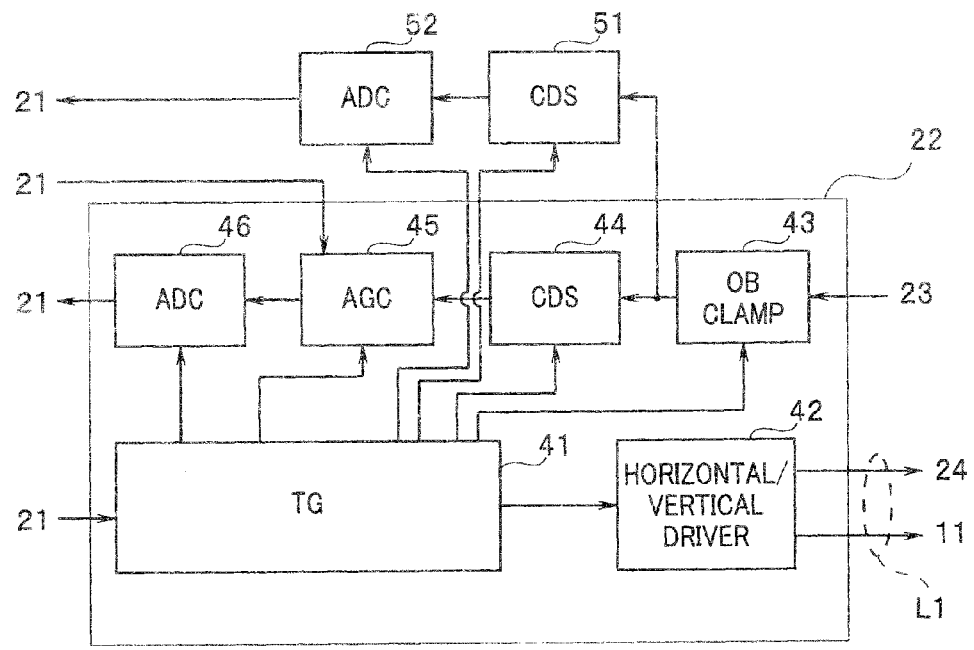
FIG. 11 is a block diagram showing configurations of the AFE section 22 and a temperature detecting section, according to a fourth embodiment of the present invention.

FIG. 11 is a block diagram showing configurations of the AFE section 22 and the temperature detecting section, according to the present embodiment. In FIG. 11, the same components as in FIG. 2 are assigned with the same reference signs, the description thereof will be omitted, and only different components will be described.

The output of the OB clamp circuit 43 of the AFE section 22 is inputted to a second CDS circuit 51. In the CDS circuit 51, correlated double sampling as will be described later is performed, and a result signal thereof is outputted to an ADC circuit 52. The ADC circuit 52 converts the inputted signal into digital data, and outputs the digital data to the CPU 21. The CDS circuit 51 and the ADC circuit 52 configure a temperature detecting section. A predetermined timing signal is inputted to each of the CDS circuit 51 and the ADC circuit 52 from the TG 41.

Figure 12:
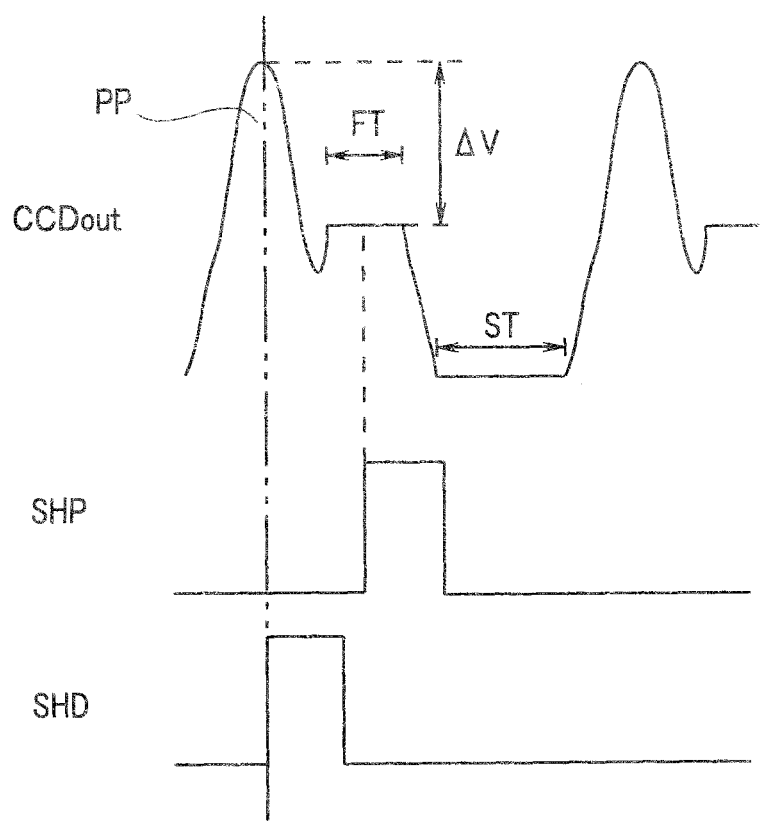
FIG. 12 is a waveform chart showing a relationship of the output signal CCDout of the CCD 11, the SHP signal and the SHD signal, for explaining correlated double sampling that is executed in a CDS circuit 51, according to the fourth embodiment of the present invention.

FIG. 12 is a waveform chart showing a relationship of the output signal CCDout of the CCD 11, the SHP signal and the SHD signal, for explaining correlated double sampling that is executed in the CDS circuit 51.

The second SHD signal is inputted to the CDS circuit 51 from the TG 41 at timing delayed from the reset gate signal RG. By the second SHD signal, a voltage of the peak value of the through pulse signal PP is clamped. The second SHP signal is inputted to the CDS circuit 51 from the TG 41 at the same timing as the SHP signal of the CDS circuit 44.

Accordingly, by the second SHP signal and the second SHD signal, a potential difference ΔV shown by the dotted line is obtained, and the potential difference ΔV is inputted to the ADC circuit 52, in FIG. 12.

Here, the potential difference ΔV changes in response to the temperature of the CCD 11 which is an image pickup device. Accordingly, a relationship of the potential difference ΔV and the temperature is obtained in advance by measurement or calculation, and is stored in the memory section 29 in advance. For example, the relationship is stored in the memory section 29 as table data in which information of the temperature at each ΔV is registered.

Namely, the temperature is determined and detected based on a difference between the potential of the peak value of the through pulse portion PP on which the reset gate signal RG is superimposed in the output signal CCDout of the CCD 11 which is an image pickup device, and the reference potential.

When the CPU 21 receives value data of the detected potential difference ΔV, the CPU 21 refers to the table data stored in the memory section 29, and reads the temperature information corresponding to the potential difference ΔV, whereby the CPU 21 can detect the temperature of the CCD 11.

The CPU 21 adjusts the pulse width of the reset gate signal RG in response to the detected temperature, as in the endoscope apparatus of the first embodiment described above.

As a result, the reference potential can be sampled and held stably in the CDS circuit 44, as a result of which, amplification noise and reset noise are properly removed, and high endoscope image quality with less noise can be obtained.

(Modification)

The present modification restricts the peak value of the reset gate signal RG so that the peak value does not become a predetermined value or more, based on the peak value of the through pulse signal PP which is clamped in the second CDS circuit 51 in the fourth embodiment. The present modification is applicable additionally to the first to the fourth embodiments described above.

In the fourth embodiment, the temperature is detected based on the potential difference ΔV which is obtained by the second CDS circuit 51, whereas in the present modification, the peak value of the reset gate signal RG is restricted so as not to be the predetermined value or more based on the peak value of the through pulse signal PP which is clamped in the second CDS circuit 51.

A circuit configuration is the same as in the fourth embodiment, but here, only the peak value of the through pulse signal PP which is clamped based on the SHD signal is clamped in the ADC circuit 52, and is outputted to the CPU 21.

The CPU 21 determines whether or not the peak value of the through pulse signal PP from the ADC circuit 52 becomes a preset threshold value or more, and when the peak value of the through pulse signal PP becomes the preset threshold value or more, the CPU 21 reduces the peak value of the reset gate signal RG by a predetermined amount, and fixes the peak value at a value reduced by the predetermined amount.

Figure 13:
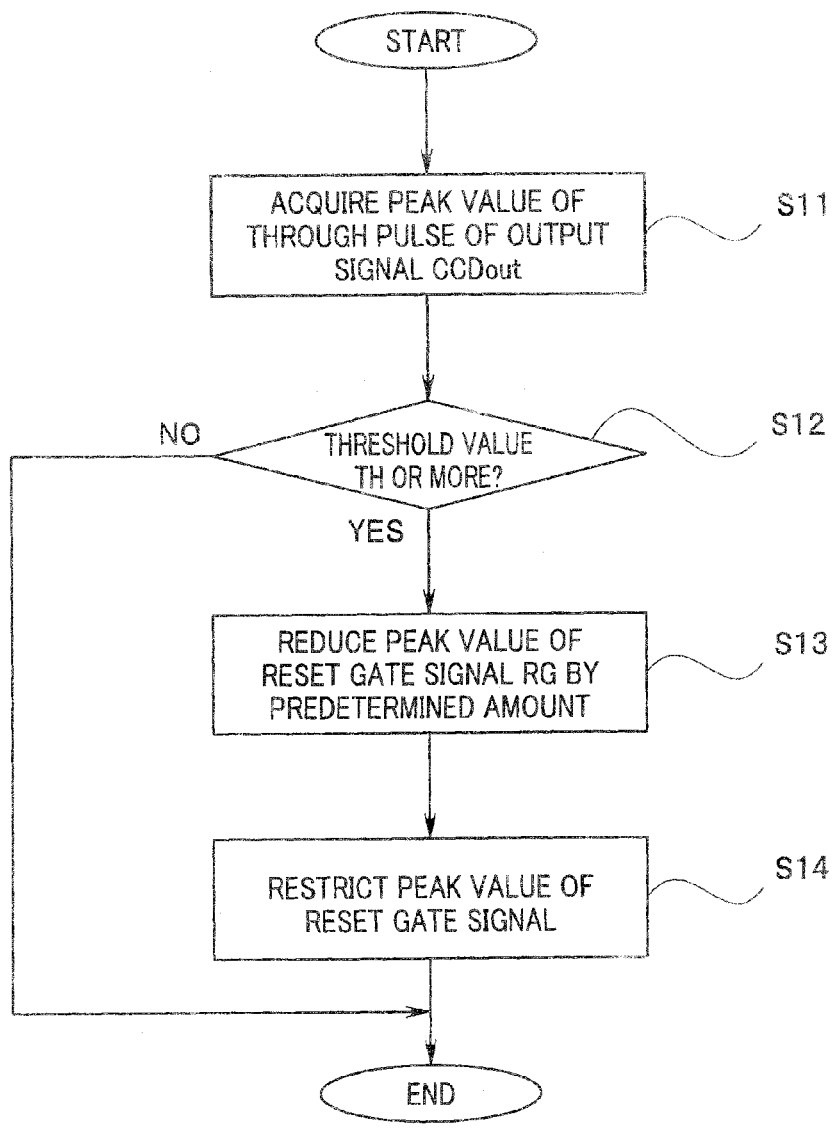
FIG. 13 is a flowchart showing an example of a flow of peak value restriction processing, according to a modification of the first to the fourth embodiments of the present invention.

FIG. 13 is a flowchart showing an example of a flow of the peak value restriction processing according to the present modification. The CPU 21 acquires the peak value of the through pulse of the output signal CCDout which is clamped by the second CDS 51 (S11).

The CPU 21 determines whether or not the acquired peak value is a predetermined threshold value TH or more (S12), and when the acquired peak value is the predetermined threshold value TH or more (S12: YES), the CPU 21 reduces the peak value to a value smaller by a predetermined amount than the present peak value of the reset gate signal RG (S13).

After S13, the CPU 21 fixes the peak value of the reset gate signal RG to the peak value reduced in S13, and restricts the peak value (S14). By the processing of S14, the CPU 21 restricts the peak value of the reset gate signal RG which is outputted from the waveform shaping circuit 24 so that the peak value of the reset gate signal RG does not become the peak value of the value reduced in S13 or more.

Namely, the processing of S12 and S13 configures a peak value restricting section that restricts the peak value of the reset gate signal RG by reducing the peak value of the reset gate signal RG by the predetermined amount so that the peak value of the reset gate signal RG does not become the reduced peak value or more when the peak value of the through pulse PP of the output signal CCDout of the CCD 11 which is an image pickup device becomes the predetermined threshold value TH or more.

Accordingly, in the respective first to fourth embodiments, the peak value of the reset gate signal RG which is outputted is restricted by addition of the function of the present modification.

Note that if the acquired peak value is not the predetermined threshold value TH or more (S12: NO), no processing is performed.

As above, according to the endoscope apparatuses of the respective embodiments and the modification described above, the feedthrough time period of the output signal of the image pickup device is stably ensured irrespective of the temperature change, as a result of which, amplification noise and reset noise are removed, and high endoscopie image quality with less noise can be obtained.

The present invention is not limited to the embodiments described above, and various modifications, alterations and the like can be made within the range without departing from the gist of the present invention.

What is claimed is:

1. An endoscope apparatus comprising:
   an insertion portion having an image pickup device in a distal end portion;
   a main body portion;
   a drive circuit that outputs a drive signal that drives the image pickup device; and
   a changing section that changes at least one of a pulse width and a peak value of a reset gate signal included in the drive signal, in response to a temperature of a vicinity of the image pickup device or the main body portion, such that a shape of a waveform of a signal output by the image pickup device driven by the drive signal is changed.

2. The endoscope apparatus according to claim 1, wherein the reset gate signal is a horizontal synchronization signal of the image pickup device.

3. The endoscope apparatus according to claim 2, wherein the reset gate signal is a signal that is outputted by being superimposed on an output signal of the image pickup device.

4. The endoscope apparatus according to claim 1, wherein the image pickup device is a charge coupled device.

5. The endoscope apparatus according to claim 1, further comprising:
   a storage section in which a change value or a correction value for changing said at least one of the pulse width and the peak value of the reset gate signal included in the drive signal, corresponding to the temperature, is stored,
   wherein the changing section refers to the storage section, reads the change value or the correction value corresponding to the temperature, and changes said at least one of the pulse width and the peak value of the reset gate signal, based on the change value or the correction value that is read.

6. The endoscope apparatus according to claim 1, further comprising a temperature sensor which detects the temperature.

7. The endoscope apparatus according to claim 6, wherein the temperature sensor is provided in the vicinity of the image pickup device to detect the temperature of the vicinity of the image pickup device, or is provided at the main body portion to detect the temperature of the main body portion.

8. The endoscope apparatus according to claim 1, wherein the temperature is determined based on a difference between a potential of a peak value of a through pulse portion on which the reset gate signal is superimposed, in an output signal of the image pickup device, and a reference potential.

9. The endoscope apparatus according to claim 1, further comprising:
   a peak value restricting section that reduces the peak value of the reset gate signal by a predetermined amount and restricts the peak value so that the peak value of the reset gate signal does not become the reduced peak value or more, when a peak value of a through pulse of an output signal of the image pickup device becomes a predetermined threshold value or more.

10. The endoscope apparatus according to claim 1, further comprising:
    a storage section in which first pulse width change data in accordance with a first temperature range, and second pulse width change data in accordance with a second temperature range lower than the first temperature range, are stored; and
    a temperature sensor that detects the temperature,
    wherein the changing section reads, based on the temperature detected by the temperature sensor, one of the first pulse width change data and the second pulse width change data corresponding to the detected temperature from the storage section, and changes the pulse width of the reset gate signal based on the read pulse width change data.

11. The endoscope apparatus according to claim 10, wherein a pulse width according to the second pulse width change data is set narrower than a pulse width according to the first pulse width change data.

12. The endoscope apparatus according to claim 1, wherein the changing section changes the pulse width of the reset gate signal such that the pulse width of the reset gate signal when the temperature is in a first range is narrower than the pulse width of the reset gate signal when the temperature is in a second range higher than the first range.

13. The endoscope apparatus according to claim 1, further comprising:
    a storage section in which first peak value change data in accordance with a first temperature range, and second peak value change data in accordance with a second temperature range lower than the first temperature range, are stored; and
    a temperature sensor that detects the temperature,
    wherein the changing section reads, based on the temperature detected by the temperature sensor, one of the first peak value change data and the second peak value change data corresponding to the detected temperature from the storage section, and changes the peak value of the reset gate signal based on the read peak value change data.

14. The endoscope apparatus according to claim 13, wherein a peak value according to the second peak value change data is set lower than a peak value according to the first pulse width change data.

15. The endoscope apparatus according to claim 1, wherein the changing section changes the peak value of the reset gate signal such that the peak value of the reset gate signal when the temperature is in a first range is lower than the peak value of the reset gate signal when the temperature is in a second range higher than the first range.

* * * * *